United States Patent [19]

Maiden

[11] Patent Number: 4,500,207

[45] Date of Patent: Feb. 19, 1985

[54] NON-DISPERSIVE OPTICAL DETERMINATION OF GAS CONCENTRATION

[75] Inventor: Adrian J. Maiden, Stockport, England

[73] Assignee: Ferranti, PLC, England

[21] Appl. No.: 440,040

[22] Filed: Nov. 8, 1982

[30] Foreign Application Priority Data

Nov. 14, 1981 [GB] United Kingdom ............ 8134389

[51] Int. Cl.³ .......................................... G01N 21/61
[52] U.S. Cl. .................................. 356/409; 250/343; 356/51; 356/437
[58] Field of Search ............... 250/343; 356/51, 434, 356/437, 409

[56] References Cited

U.S. PATENT DOCUMENTS

| | | | |
|---|---|---|---|
| 3,679,899 | 7/1972 | Dimeff | 250/343 |
| 3,728,540 | 4/1973 | Todd et al. | 250/343 |
| 3,899,252 | 8/1975 | Dimeff | 250/343 |
| 3,901,820 | 8/1975 | Wood | 250/343 |
| 3,922,551 | 11/1975 | Williams | 250/343 |
| 4,163,899 | 8/1979 | Burough | 250/343 |

FOREIGN PATENT DOCUMENTS

| | | |
|---|---|---|
| 849983 | 9/1960 | United Kingdom . |
| 1465563 | 2/1977 | United Kingdom . |
| 1523605 | 9/1977 | United Kingdom . |
| 1531844 | 11/1978 | United Kingdom . |

Primary Examiner—F. L. Evans
Attorney, Agent, or Firm—Dennis P. Clarke

[57] ABSTRACT

Apparatus (FIG. 1) for non-dispersive optical determination of the concentration of an identifiable gas, such as a hydrocarbon, in a mixture such as atmospheric air comprises a sample chamber 13 to contain a sample of the mixture, a source 21 of IR radiation at a wavelength absorbed by the gas beamed through the sample chamber to a detector 22 and transducer means to change the gas pressure within the chamber to determine the change in radiation intensity detected at different pressures. One wall of the sample chamber is formed by a flexible diaphragm 25 driven by a voice-coil type transducer 26 whereby the pressure is switched repetitively between the values above and below atmospheric. Atmospheric gas is admitted to the chamber by a porous plug 24 which restricts flow to a low level permitting a pressure change in the chamber. Absorption by the gas relates the intensity of source radiation $I_S$ and measured radiation $I_M$ by $I_M \propto I_S \cdot e^{-\alpha_o \cdot g \cdot p \cdot x}$ where x is the radiation path length through the sample, $\alpha_o$ is a constant, p the total pressure of the gas mixture and g the concentration of the hydrocarbon gas. By measuring intensity at different pressure involving a change $\Delta p$ and a fractional change in intensity of measured radiation $\Delta I/I$, the gas concentration g is determined by applying the relationship:- $g = -\Delta I/(I \cdot \Delta p \cdot \alpha_o \cdot x)$.

13 Claims, 5 Drawing Figures

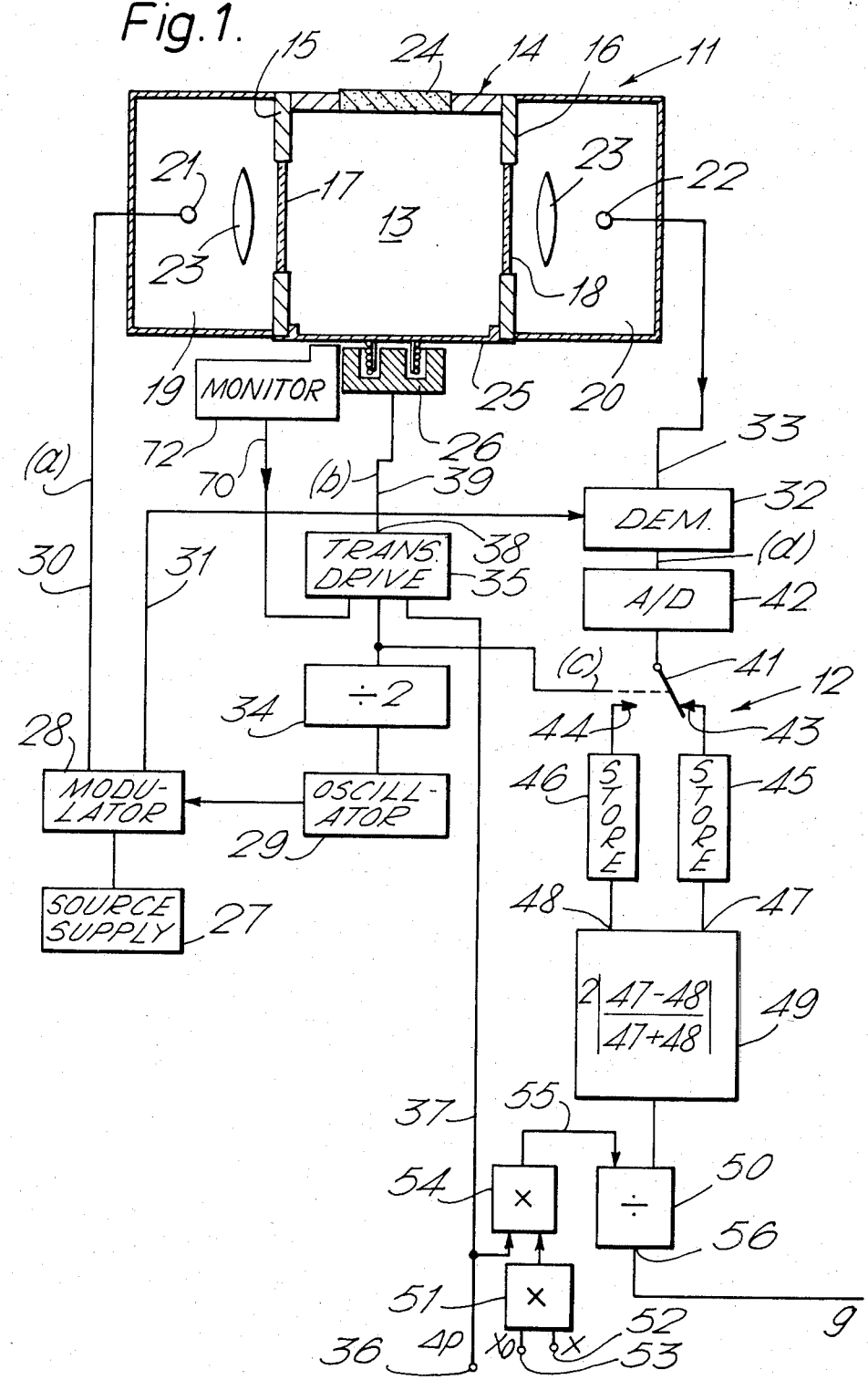

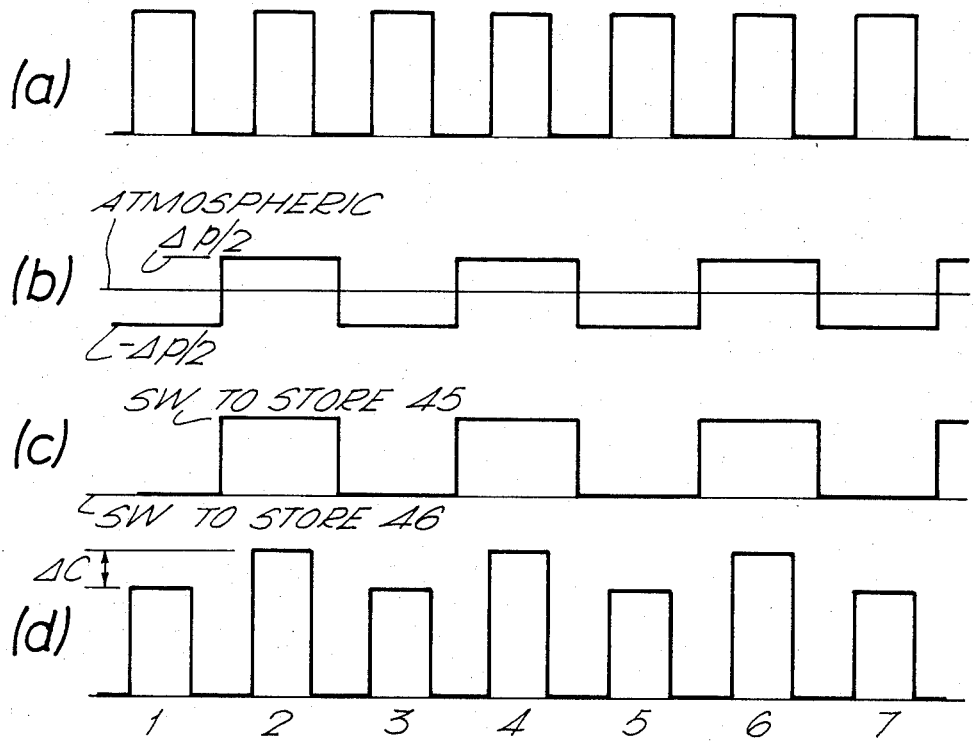

NON-DISPERSIVE OPTICAL DETERMINATION OF GAS CONCENTRATION

This invention relates to the determination of the concentration of a gas component identifiable in a gaseous atmosphere by non-dispersive optical analysis.

Spectroanalysis apparatus commonly has an operating scheme based upon Beer's law relating the variation in intensity of optical radiation, emitted by a source at a wavelength absorbed by a specific gas, with passage through a gas mixture containing the gas. This may be conveniently stated as $$I_M = I_S \cdot f(T) \cdot e^{-\alpha \cdot x} \qquad (1)$$

where $I_M$ is measured intensity, $I_S$ the source intensity, $f(T)$ a function related to the transmissivity of the gas mixture container, $x$ is the path length of radiation through the gas mixture and $\alpha$ is the absorption coefficient for the specific gas by which it is identifiable. The absorption coefficient $\alpha$ may be defined by the relationship $$\alpha = \alpha_o \cdot g \cdot p. \qquad (2)$$

where $\alpha_o$ is a constant, characteristic of the gas, $p$ the total pressure of the gas mixture and $g$ the concentration in the mixture of the gas of interest.

Normally the apparatus also functions to pass through the gas mixture radiation at a wavelength not absorbed by the specific gas, whereby the relationship obeyed is $$I_{M'} = I_{S'} \cdot f(T) \qquad (3)$$

enabling the expression to be obtained from equations (1) and (3)

$$e^{-\alpha \cdot x} = (I_M/I_{M'}) \cdot (I_{S'}/I_S) \qquad (4)$$

from which $\alpha$, and thus $g$, can be derived.

The intensity of emission at the two frequencies may be assumed equal and disappear from equation (4) or may be measured by detecting source radiation at the two wavelengths passed along reference paths to the same or other detection means. Examples of apparatus employing such a system are to be found in British Patent Specification Nos. 1,531,844, 1,523,605 and 1,465,563.

While the apparatus described therein have differences peculiar to individual applications they all demonstrate the optical and/or mechanical complexity of such apparatus, both in terms of filtering radiation in order to achieve measurement made at different radiation wavelengths and of achieving a plurality of optical paths.

British Patent Specification No. 849,983 describes an arrangement wherein the use of a plurality of optical paths and operation at different radiation wavelengths is avoided by employing the relationship between radiation intensities of the same wavelength at different gas preserves rather than at different wavelengths for gas of the same pressure.

The apparatus described therein by which this is achieved is for use with a wide variety of contained gases and conventional in that a sample chamber is provided with inlet and outlet values by which gas is supplied to and removed from the sample chamber.

When the gas is in fact a surrounding atmosphere then the construction may be simplified and it is an object of the present invention to provide apparatus for non-dispersive optical determination of the concentration of an identifiable gas in an atmosphere, and a method of such determination, which is simpler than known arrangements.

According to a first aspect of the present invention apparatus for non-dispersive optical determination of the concentration of an identifiable gas in an atmosphere comprises a sample chamber arranged to communicate with the atmosphere by flow limiting means in the form of a plug of porous material operable to limit the rate of gas flow between the chamber and atmosphere to a value whereby after a pressure change is induced in the chamber and for a measurement time period thereafter there is no substantial restoration of gas pressure within the sample chamber towards atmospheric, transducer means operable to change the pressure of the gas mixture in the sample chamber by a predetermined amount between first and second pressures, a source of a beam of radiation at a wavelength absorbed by the identifiable gas only of the mixture, window means by which the radiation is passed through the sample chamber, a detector responsive to radiation at said wavelength after passage through the sample chamber to produce a signal related to the intensity level of the radiation detected, and signal processing means operable to derive a signal representing the fractional change in intensity ($\Delta I/I$) of the detected radiation due to the pressure change in the sample chamber and calculate from said derived signal, the chamber pressure change ($\Delta p$), radiation path length through the gas mixture ($x$) and an absorption constant characteristic of the specific gas ($\alpha_o$), a representation of the gas concentration $g$ in accordance with the formula:

$$g = -\Delta I/(I \cdot \Delta p \alpha_o \cdot x).$$

According to a second aspect of the present invention a method of non-dispersive optical determination of the concentration of an identifiable gas in the atmosphere comprises holding a sample of the atmospheric gas mixture in a sample chamber in communication with the atmosphere by means of a porous plug operable to limit the rate of gas flow between the atmosphere and the sample chamber to a level at which a pressure change may be effected and radiation intensities measured before any significant flow of gas through the plug restores the pressure within the chamber to atmospheric, passing radiation at a wavelength absorbed by the identifiable gas through the sample chamber, detecting the intensity of radiation at said wavelength received after passage through the chamber with the gas mixture at a first pressure, changing the pressure in the chamber by a predetermined amount ($\Delta p$) to a second pressure, detecting the intensity of radiation at said wavelength after passage through the chamber with the gas mixture at the second pressure, determining the fractional change in intensity of detected radiation ($\Delta I/I$) consequent upon the change of gas pressure, and calculating the value of the gas concentration $g$ of the identifiable gas in accordance with the formula:

$$g = -\Delta I/(I \cdot \Delta p \cdot \alpha_o \cdot x)$$

where x is the path length of the radiation through the sample and $\alpha_o$ is an absorption coefficient constant for the identifiable gas.

The above formula by which gas concentration g is determined is derived from the Beer's law equations (1) and (2) quoted earlier. From equation (1) it can be shown that $$\Delta I/\Delta p = I \cdot -d\alpha/dp \cdot x \tag{5}$$

and from equation (2) $d\alpha/dp = \alpha_o \cdot g$, so that $$\Delta I/\Delta p = -I \cdot \alpha_o \cdot x \cdot g, \text{ and}$$
$$g = -(\Delta I/I) \cdot 1/(\alpha_o \cdot x \cdot \Delta p), \text{ or}$$
$$g = -\Delta I/(I \cdot \Delta p \cdot \alpha_o \cdot x) \tag{6}$$

It will be appreciated that the term $\Delta I/I$ is independent of the absolute value of the intensity measured and thus of the transmissivity of cell windows f(T).

Embodiments of the present invention, hereinafter referred to as a gas analyser will now be described by way of example, in which:

FIG. 1 is a schematic representation of a preferred form of gas analyser for the determination of the concentration of a hydrocarbon gas in the atmosphere, and FIGS. 2(a) to 2(d) show representations of waveforms of signals appearing at correspondingly labelled points in the circuit of FIG. 1.

Referring to FIG. 1 a gas analyser 10 comprises a sample chamber portion 11 and a control and signal processing circuit portion 12.

The sample chamber portion 12 comprises a chamber enclosure 13 bounded by walls 14. Opposite walls 15, 16 each contain a window 17, 18 respectively of glass, quartz or other suitable material transmissive of optical radiation in the infra-red part of the spectrum and separate the sample chamber from enclosures 19, 20 in which are contained an infra-red optical source 21 and a photodetector 22 respectively. The chambers 19, 20 also contain optical focussing elements 23 by which infra-red radiation from the source 20 is directed through the window 15, chamber 13, window 18 and on to detector 22.

The apparatus is intended primarily for the detection in the atmosphere of small and potentially explosive concentrations of hydrocarbon gases which as a family absorb infra-red radiation with a wavelength of 2350 nm and the source 21 is arranged to emit radiation in a narrow band around this wavelength.

The enclosure wall 14 contains an arrangement by which atmospheric gas can communicate with the enclosure and comprises a plug 24 of porous sintered metal such as stainless steel through which gases can diffuse readily but only at a low rate of transfer.

Another portion of the enclosure wall 14 comprises a diaphragm 25 which is reciprocable by a transducer 26 to change the volume of the chamber 13. The transducer is conveniently electromagnetic such as provided by a loudspeaker voice-coil and magnet arrangement.

If the diaphragm is at rest (transducer unpowered), or maintained at any position for a considerable length of time the gas pressure within the chamber will equalise with atmospheric pressure by virtue of communication through the porous plug 14. If the diaphragm is moved to a new position by the transducer the volume of the chamber is varied and the pressure of the gas mixture therein correspondingly changed. After a while the pressure will again equalise with the atmosphere because of the porous plug but initially the pressure may be assumed to have changed by an amount related to the movement of the transducer 26 and diaphragm and which may be calibrated during production or before operation by equating positional changes of the transducer with pressure changes measured within the chamber by pressure measuring instruments.

If the diaphragm is oscillated about a rest position the mean pressure within the chamber will remain at atmospheric pressure while the instantaneous pressure varies between first and second pressures above and below this for each change of diaphragm position. In this mode of operation the intensity does not vary from a "stable" level to a unidirectional pressure change but varies between two levels each due to a pressure change of $\Delta p/2$ from atmospheric.

Referring also to the circuit portion 12, the source 21 is powered by a supply 27, the output of which passes to the source by way of a modulator 28, operable under the control of a square wave oscillator 29, to produce an intermittent or 100 percent modulated source supply on line 30 having the waveform shown in FIG. 2(a) and corresponding modulation of the intensity of radiation emitted by the source. The modulator also has an output 31 connected to a synchronous detector 32 arranged to receive signals from photodetector 22 on line 33.

The output of modulation oscillator 29 is also applied to a divide-by-two circuit 34 and thence to a control input of a drive circuit 35 of the transducer 26. The transducer undergoes a displacement proportional to the voltage applied, which voltage level is set by a signal representing the desired pressure change $\Delta p$ (or $\pm p/2$) applied from adjustable setting means (not shown) by way of an input terminal 36 and line 37. An output terminal 38 of the transducer drive circuit is connected to the transducer by line 39 and provides a drive voltage switched in polarity by the input from divider 34 at half the modulation frequency of the source, as shown by waveform FIG. 2(b). The output terminal divide-by-two circuit 34 is also connected to control the state of a change-over switch shown schematically at 41.

The photodetector 22 receives radiation modulated at one frequency by the source modulator 28 and, if a hydrocarbon gas is present to absorb some of the radiation at another frequency (half of said one frequency) by pressure variations in the sample chamber. The photodetector signal is demodulated by synchronous detector 32 which produces a pulse train signal having the waveform shown at FIG. 2(c) corresponding to the pulsed source emissions, the amplitude of each pulse being directly proportional to the intensity of the radiation received from the corresponding pulsed emission.

Processing of the signals is conveniently carried out in digital form and the signal (c) produced by demodulator 32 is applied to an A/D converter 42 and then to the common terminal of change-over switch 41.

The output terminals 43, 44 of the switch 41 are connected respectively to inputs of store 45, 46 each of which is capable of storing a representation of the amplitude of one of the received radiation pulses. The outputs of stores 45, 46 are fed to inputs 47, 48 respectively of a processing circuit arranged to read the stores and perform the operation 2·(input 47 − input 48)/(input 47 + input 48); that is $2\Delta I/(I_{p1} + I_{p2})$ where $(I_{p1} + I_{p2})/2$ represents the average intensity signal received by the detector. The output of the processing circuit is fed to a numerator input of a division circuit 50.

A multiplication circuit 51 is arranged to receive signals at inputs 52 and 53. The signal applied to input 52 represents the length x of the radiation path through the sample chamber and is fixed for the apparatus. The signal applied to input 53 represents the absorption coefficient constant $\alpha_o$ which is for the family of hydrocarbon gases of interest. The output of the multiplication circuit 51 is applied to one input of a similar multiplication circuit 54, the other input being connected to receive signals representing the pressure change $\Delta p$ from input terminal 36. The output of multiplication circuit 54 thus represents the product $(\Delta p \cdot \alpha_o \cdot x)$ which is applied by line 55 to a denominator input of division circuit 50. The output of the division circuit 50 represents the result of the division of the two inputs and is made available at output terminal 56.

Considering operation of the apparatus with a hydrocarbon gas component present in the atmospheric gas mixture in the sample chamber, it will be seen with reference to the waveforms of FIG. 2 that the pressure in variations between $\pm \Delta p/2$ with respect to atmospheric pressure (that is with the diaphragm 25 in a stable rest position) occur at half the modulator frequency of the radiator emissions so that considering sharp pulse-like transitions, alternate radiation pulses are transmitted through the sample chamber at higher and lower gas pressures. It will be seen from equation (1) that for a pressure dependent $\alpha$ the intensity of received radiation will decrease with increasing pressure so that the signal detected and demodulated will comprise a series of pulses (d) alternating in amplitude between a lower level, when the gas sample is at a higher pressure, and a higher level, when the gas sample is at a lower pressure, the difference in level between adjacent pulses representing the intensity difference $\Delta I$ and average level of the pulses the intensity I with respect to which the change is measured.

Considering the received pulses of waveform (d) to be numbered 1 ... 7 etc. and the change-over switch initially connected to store 45, the first detected pulse 1 is digitised and applied to store 45, then the switch 41 changes state in synchronism with the pressure change in the chamber so that the second detected pulse 2 is digitised and applied to store 46. When both stores have signals therein the signals are fed to the input 47, 48 respectively of processing circuit 49 which determines the value $\Delta I/I$, which is applied to one input of division circuit 51 and divided by the other input $(\Delta p \cdot \alpha_o \cdot x)$ to give a value for g.

The switch 41 is operated by the next pressure pulse so that the next received detected pulse 3 is fed to store 45 to write the new value of pulse 3 in place of the previously stored value of pulse 1, and as both stores are full the processing circuit 49 reads them and this time determines the value of $\Delta I/I$ for pulses 2 and 3. After determination of g the switch 41 is operated by the next pressure pulse so that received pulse 4 is fed to store 46 and read with previously stored pulse 3 from store 45 to determine a new value for $\Delta I/I$.

The output terminal 56 thus provides a succession of digital representations of the concentration of a hydrocarbon gas in the atmospheric mixture within the sample chamber. As referred to above in connection with equation (6) the computation is independent of the absolute value of source intensity and of the transmissivity of windows 17 and 18 so that the apparatus is unaffected by ageing of the source or by a build up of radiation absorbing film on the windows both within and without the sample chamber. The signals may be converted to analog form for continuous display or stored or otherwise used in digital form. The output signals may be applied to a threshold device set to a level above which the gas concentration is hazardous, in order to initiate an alarm conditions should the threshold be exceeded.

The above described embodiment represents one particular form the apparatus may take and is open to modification and changes some of which will be self evident. For example, the source 21 modulated by switching is conveniently an L.E.D. The diode may be arranged to emit radiation at the desired wavelength or to emit at a different wavelength to illuminate a phosphor which does emit at the desired wavelength. Instead of being modulated by switching on and off the source may be continuously emissive and the radiation therefrom modulated by an electrical or mechanical shutter, such as a chopper disc. The modulation may be other than 100 percent effected by switching or chopping and signals received may be processed other than digitally. Also in the embodiment described the modulation of chamber pressure is at half the rate of the source modulation which provides received pulses of alternate different amplitudes for convenient processing with successive pulses. It will be appreciated that the pressure modulation may be carried out at a slower rate, a number of cycles of the sources modulation at each pressure level being used, e.g. averaged, in the computation of g.

The transducer 26 may be an electromagnetic design of other than the voice-coil configuration shown or may be a non-electromagnetic type e.g. piezoelectric.

One consideration for electromagnetic transducers and diaphragm arrangement is the variation of induced pressure changes with aging of components. A feedback arrangement may be employed to derive a signal related to diaphragm movement and apply the signal on line 70 (FIG. 1) to transducer drive circuit 35 to control the amplitude of the device signal applied to the transducer to maintain a necessary movement to give a demanded pressure change. The feedback arrangement may comprise a position sensor or monitor means 72 (FIG. 1) responsive to diaphragm or transducer position or in the case of an electromagnetic coil, by a separate sensing coil or electrical apparatus to monitor the transducer impedance.

The processing of signals may be performed as shown by circuit elements having the specific functions outlined above in either digital or analog form.

The magnitude of the pressure change $\Delta p$ is largely a matter of choice. The accuracy with which $\Delta p$ is effected and with which $\Delta I$ is measured increases with the magnitude of the pressure change but a practical limitation is placed on the value by the structure of the sample chamber and any tendency of the pressure change to distort the walls 15, 16 and/or the windows 17, 18 and change the optical path length through the chamber from the assumed value x employed in the signal processing.

The apparatus described in the above embodiments has assumed determination of the concentration of hydrocarbon gases which absorb infra-red radiation at a specific wavelength. It will be appreciated that the apparatus and method employed is suitable for determination of concentration of any gas component for which an absorption wavelength can be determined and radiation emitted and identifiable by absorption of said radiation by the gas.

I claim:

1. Apparatus for non-dispersive optical determination of the concentration of an identifiable gas in an atmosphere comprising a sample chamber arranged to communicate with the atmosphere by flow limiting means in the form of a plug of porous material operable to limit the rate of gas flow between the chamber and atmosphere to a value whereby after a pressure change is induced in the chamber and for a time period thereafter there is no substantial restoration of gas pressure within the sample chamber towards atmospheric, transducer means operable to change the pressure of the gas mixture in the sample chamber by a predetermined amount between first and second pressures, a source of a beam of radiation at a wavelength absorbed by the identifiable gas only of the mixture, window means by which the radiation is passed through the sample chamber, a detector responsive to radiation at said wavelength after passage through the sample chamber to produce a signal related to the intensity level of the radiation detected, and signal processing means operable to derive a signal representing the fractional change in intensity ($\Delta I/I$) of the detected radiation due to the pressure change in the sample chamber and calculate from said derived signal, the chamber pressure change ($\Delta p$), radiation path length through the gas mixture ($x$) and an absorption constant characteristic of the specific gas ($\alpha_o$), a representation of the gas concentration g in accordance with the formula $$g = -\Delta I/(I \cdot \Delta p \alpha_o \cdot x).$$

2. Apparatus as claimed in claim 1 in which the plug is formed of stainless steel.

3. Apparatus as claimed in claim 1 in which source is arranged to emit a beam modulated in intensity.

4. Apparatus as claimed in claim 3 in which the beam is 100 percent modulated by permitting radiation emitted by the source to pass through the sample chamber only intermittently.

5. Apparatus as claimed in claim 4 in which the beam is modulated by switching on and off repetitively the power supply to the source.

6. Apparatus as claimed in of claim 1 in which the transducer means is arranged to modulate the gas pressure within the sample chamber between two values at each of which the intensity of radiation passed through the sample chamber is detected.

7. Apparatus as claimed in claim 6 in which the transducer is arranged to change the pressure periodically between values equally above and below atmosphere pressure.

8. Apparatus as claimed in claim 1 in which the transducer means includes a diaphragm forming part of the wall of the sample chamber and movable to change the volume of the chamber to change the pressure of the gas therein and drive means operable to move at least part of the diaphragm.

9. Apparatus as claimed in claim 8 in which the transducer drive means comprises an electromagnetic voice-coil-like assembly fixed to the diaphragm and movable in a magnetic field by a drive signal applied thereto to produce a pressure change in the chamber in accordance with the magnitude of the drive signal and the impedance of the transducer means.

10. Apparatus as claimed in claim 9 in which the transducer means includes monitor means operable to monitor displacement of the diaphragm in response to a drive signal to provide a correction to the drive signal to effect a demanded diaphragm displacement.

11. A method of non-dispersive optical determination of the concentration of an identifiable gas in the atmosphere comprising holding a sample of the atmospheric gas mixture in a sample chamber in communication with the atmosphere by means of a porous plug operable to limit the rate of gas flow between the atmosphere and the sample chamber to a level at which a pressure change may be effected and radiation intensities measured before any significant flow of gas through the plug restores the pressure within the chamber to atmospheric, passing radiation at a wavelength absorbed by the identifiable gas through the sample chamber, detecting the intensity of radiation at said wavelength received after passage through the chamber with the gas mixture at a first pressure, changing the pressure in the chamber by a predetermined amount ($\Delta p$) to a second pressure, detecting the intensity of radiation at said wavelength after passage through the chamber with the gas mixture at the second pressure, determining the fractional change in intensity of detected radiation ($\Delta I/I$) consequent upon the change of gas pressure, and calculating the value of the gas concentration g of the identifiable gas in accordance with the formula:

$$g = -\Delta I/(I \cdot \Delta p \cdot \alpha_o \cdot x)$$

where $x$ is the path length of the radiation through the sample and $\alpha_o$ is an absorption coefficient constant for the identifiable gas.

12. A method as claimed in claim 11 in which the pressure is changed repetitively between two alternate values disposed about atmospheric pressure and one measurement of gas concentration is made subsequent to each pressure change.

13. A method as claimed in claim 11 or claim 12 in which the sample chamber pressure is changed by changing the volume of the sample chamber while maintaining the mass of gas therein substantially constant.

* * * * *